United States Patent [19]
Grandy et al.

[11] Patent Number: 5,658,783
[45] Date of Patent: Aug. 19, 1997

[54] MAMMALIAN METHADONE-SPECIFIC OPIOID RECEPTOR GENE AND USES

[75] Inventors: David K. Grandy; James R. Bunzow, both of Portland, Oreg.; Olivier Civelli, Aesch, Switzerland

[73] Assignee: State of Oregon, Acting by and Through the Oregon State Board of Higher Education on Behalf of the Oregon Health Sciences University, a non-profit organization, Portland, Oreg.

[21] Appl. No.: 149,093

[22] Filed: Nov. 8, 1993

[51] Int. Cl.$^6$ .............................. C12N 15/12; C12N 5/10
[52] U.S. Cl. ................ 435/325; 435/252.3; 435/254.11; 435/320.1; 435/69.1; 435/365; 435/364; 435/367; 435/361; 435/356; 536/23.5; 536/24.3
[58] Field of Search ...................... 536/23.1, 24.3, 536/23.5; 435/69.1, 240.2, 320.1, 252.3, 254.11

[56] References Cited

PUBLICATIONS

Chen et al., 1993, "Molecular Cloning and Functional Expression of a μ-Opioid Receptor from Rat Brain", *Molec. Pharmacol.* 44: 8–12.
Yasuda et al., 1993, "Cloning and functional comparison of κ and δ opioid receptors from mouse brain", *Proc. Natl. Acad. Sci. USA* 90: 6736–6740.
Bzdega et al., 1993, "Regional expression and chromosomal location of the δ opiate receptor gene", *Proc. Natl. Acad. Sci. USA* 90: 9305–9309.
Brownstein, 1993, "A brief history of opiates, opioid peptidfes amnd opioid receptors", *Proc. Natl. Acad. Sci. USA* 90: 5391–5393.
DiChara & North, 1992, "Neurobiology of opiate abuse", *Trends in Phamacol. Sci.* 13: 185–193.
Maneckjie and Minna, 1992, "Nonconventional opioid binding sites mediate growth inhibitory effects of methadone on human lung cancer cells", *Proc. Natl. Acad. Sci. USA* 89: 1169–1173.

Kieffer et al., 1992, "The δ-opioid receptor: Isolation of a cDNA by expression cloning and pharmacological characterization", *Proc. Natl. Acad. Sci. USA* 89: 12048–12052.
Evans et al., 1992, "Cloning of a Delta Opioid Receptor by Functional Expression", *Science* 258: 1952–1955.
McKnight & Rees, 1991, "Opioid Recepotors and their Ligands", *Neurotransmissions* 7: 1–6.
Goldstein, 1987, "Binding selectivity profiles for ligands of multiple receptor types: focus on opiod receptors", *Trends in Pharmacol. Sci.* 8: 456–459.
Kristensen et al., Life Sciences, vol. 56, PL 45, 1995.
Fukuda et al., FEBS Letters, vol. 327, p. 311, 1993.
Wang et al., PNAS, vol. 90, p. 10230, 1993.
Reeck et al., Cell, vol. 50, 667, 1987.
Lewin, Science, vol. 237, Sep. 25, 1987.

*Primary Examiner*—Stephen G. Walsh
*Assistant Examiner*—Sally P. Teng
*Attorney, Agent, or Firm*—Banner & Allegretti, Ltd.

[57] ABSTRACT

The present invention relates to a novel mammalian methadone-specific opioid receptor protein and genes that encode a such protein. The invention is directed toward the isolation, characterization and pharmacological use of mammalian methadone-specific opioid receptor proteins. The invention specifically provides isolated complementary DNA copies of mRNA corresponding to the rat homologue or the mammalian methadone-specific opioid receptor gene. Also provided are recombinant expression constructs capable of expressing the mammalian methadone-specific opioid receptor genes of the invention in cultures of transformed prokaryotic and eukaryotic cells, as well as such cultures of transformed cells that synthesize the mammalian methadone-specific opioid receptor proteins encoded therein. The invention also provides methods for screening compounds in vitro that are capable of binding to the mammalian methadone-specific opioid receptor proteins of the invention, and further characterizing the binding properties of such compounds in comparison with known opioid receptor agonists and antagonists.

4 Claims, 10 Drawing Sheets

FIG. 1A

```
CCGAGGAGCCATTCCCAGCCGCAGCAGACCCCAATCTAGAGTGAGAGTCATTGCTCAGTCCACTGTGCTCC         71
TGCCTGCCCGCCTTTCTGCTAAGCATTGGGGTCTATTTTGCGCCCAGCTTCTGAAGAGGCTGTGTGTGCCG        142
TTGGAGGAACTGTACTGAGTGGCTTTGCAGGTGTGACAGCATGGAGTCCCTCTTTCCTGCTCCATACTGGGAG      214
                                   M  E  S  L  F  P  A  P  Y  W  E
GTCTTGCATGGCAGCCACTTTCAAGGGAACCTGTCCCTAAATGAGACCGTACCCCACCACCTGCTCCTC          286
 V  L  H  G  S  H  F  Q  G  N  L  S  L  N  E  T  V  P  H  H  L  L  L
AATGCTAGTCACAGGCAGCCTTCCTGCCCCTTGGACTCAAGGTCACCATGCGTGGCTCATCTTGGCTGTGTGC      358
 N  A  S  H  S  A  F  L  P  L  G  L  K  V  T  I  V  G  L  I  L  A  V  C
                                       I
ATCGGGGGGCTCCTGGGAACTGCCTCGTCATGTATGTCATCCTCAGGACACCCAAGATGAAGACAGCTACC        430
 I  G  G  L  L  G  N  C  L  V  M  Y  V  I  L  R  T  P  K  M  K  T  A  T
         I                                                     II
AACATTTACATATATTTAATCTGGCACTGGCTGATACCCTGGTCTTGCTAACACTGCCCTTCCAGGGCACAGAC    502
 N  I  Y  I  F  N  L  A  L  A  D  T  L  V  L  L  T  L  P  F  Q  G  T  D
     II
ATCCTACTGGGCTTCTGGCCATTGGGAAAGCACTCTGCAAGACTGTCATTGCTATGACTACTACAACATG        574
 I  L  L  G  F  W  P  F  G  K  A  L  C  K  T  V  I  A  M  T  T  T  M
                                             III
TTTACCAGCACTTTTACTCTGACCGCCATGAGCGTAGACCGCTATGTGGCTATCTGCCACCCTATCCGTGCC      646
 F  T  S  T  F  T  L  T  A  M  S  V  D  R  Y  V  A  I  C  H  P  I  R  A
   III
```

FIG. 1B

```
CTTGATGTTCGGACATCCAGCAAAGCCCAGCTGTTAATGTGGCCCATATGGGCCCTGGCTTCAGTGGTTGGT    718
 L   D   V   R   T   S   K   A   Q   A   V   N   V   A   I   W   A   L   A   S   V   V   G
                                     *                       IV

GTTCCTGTTGCCATCATGGGTTCAGCACACAAGTGGAAGAGATGAAGAGATCGAGTGCCTGGTGGAGATCCCTGCC    790
 V   P   V   A   I   M   G   S   A   Q   V   E   D   E   E   I   E   C   L   V   E   I   P   A
             IV

CCTCAGGACTATTGGGGCCCTGTATTCGCCATCTGCATCTTCTCCTTTTTCCTTCATCATCCCTGTGCTGATC    862
 P   Q   D   Y   W   G   P   V   F   A   I   C   I   F   S   F   F   I   I   P   V   L   I
                                                 V

ATCTCTGTCTGCTACAGCCTCATGATTCGACGACTTCGTGGTCTCCGGTGTCCTGCTTTCAGGCTCCCGGGAGAAG    934
 I   S   V   C   Y   S   L   M   I   R   R   L   R   G   V   R   L   L   S   G   S   R   E   K
             V

GACCGAAACCTGCGGCGTATCACTCGACTGGTGCTGGTAGTGGTGGCTGTGTTTGTGGGCTGCTGGACGCCT    1006
 D   R   N   L   R   R   I   T   R   L   V   L   V   V   A   V   F   V   G   C   W   T   P
                                                                     VI

GTGCAGGTGTTTGTCCTGGTTCAAGGACTGGGTGTTCAGCCAGGTAGTGAGACTGCAGTTGCCATCCTGCGC    1078
 V   Q   V   F   V   L   V   Q   G   L   G   V   Q   P   G   S   E   T   A   V   A   I   L   R
         VI

TTCTGCACAGCCCTGGCCTATGTCAACAGTTGTCTAATCCCATTCTCTATGCTTTCCTGGATGAGAACTTC    1150
 F   C   T   A   L   G   Y   V   H   S   C   L   N   P   I   L   Y   A   F   L   D   E   N   F
             VII
```

FIG. 1C

```
AAGGCCTGCTTTAGAAAAGTTCTGCTGTGCTTCATCCCTGCACCGGGAGATGCAGGTTTCTGATCGTGTGCGG    1222
 K  A  C  F  R  K  F  C  C  A  S  S  L  H  R  E  M  Q  V  S  D  R  V  R
                                                             *
ACGATTGCCAAGGATGTTGGCCTTGGTTGCAAGACTTCTGAGACAGTACCACGGCCAGCATGACTAGGCGTG    1294
 T  I  A  K  D  V  G  L  G  C  K  T  S  E  T  V  P  R  P  A
GACCTGCCCACATGGTGCCTGTCAGCCCACAGAGCCCATCCTACACCCAACACGGAGCTCACACAGGTCACTGC    1366
TCTCTAGGTTGACCCTGAACCTTGAGCATCTGGAGCCCTTGAATGGCTTTTCTTTTGGATCAGGATGCTCAGT    1438
CCTAGAGGAAGACC
```

FIG. 2A

```
LC132                              MESLFPAPYWEVL
Rat μ-Opioid Receptor      MDSSTGPGNTSDCSDPLAQASCSPAPGSWLNLS
Mouse δ-Opioid Receptor                    MELVPSARAELQSS
Mouse κ-Opioid Receptor            MESPIQIFRGDPGPTCSPSACLLP I
LC132    HGSHFQGNLSLLINETVPHHLLLNASHSAFLPLGLKVTIVGLILAVCIGGLLGNCL
(μ-OR)   HVDGNQSDPCGLNRTGLGGNDSLCPQTGSPSMVTAITIMALYSIVCVVGLFGNFL
(δ-OR)   PLVNLSDAFPSAGANASGSPGARSASSLALAIAITALYSAVCAVGLLGNVL
(κ-OR)   NSSSWFPNWAESDSNGSVGSEDQQLESAHISPAIPVIITAVYSVVFVVGLVGNSL
                        II
LC132    VMYVILRTPKMKTATNIYIFNLALADTLVLLTLPFQGTDILLGFWPFGKALCKTV
(μ-OR)   VMYVIVRYTKMKTATNIYIFNLALADALATSTLPFQSVNYLMGTWPFGTILCKIV
(δ-OR)   VMFGIVRYTKLKTATNIYIFNLALADALATSTLPFQSAKYLMETWPFGELLCKAV
(κ-OR)   VMFVIIRYTKMKTATNIYIFNLALADALVTTMPFQSAVYLMNSWPFGDVLCKIV
                                                IV
LC132    IAIDYYNMFTSTFTLTTAMSVDRYVAICHPIRALDVRTSSKAQAVNVAIWALASVV
(μ-OR)   ISIDYYNMFTSIFTLCTMSVDRYIAVCHPVKALDFRTPRNAKIVMVCNWILSSAI
(δ-OR)   LSIDYYNMFTSIFTLTMMSVDRYIAVCHPVKALDFRTPAKAKLIMICIWVLASGV
(κ-OR)   ISIDYYMMFTSIFTLTMMSVDRYIAVCHPVKALDFRTPLKAKIIMICIWLLASSV
```

FIG. 2B

```
                                                                         V
LC132    GVPVAIMGSAQ   VEDEEIECLVEIPAP  QDYWGPVEAICIFLFSFIIPVLIISV
(μ-OR)   GLPVMFMATTK   YRQGSIDCTLTFSHP  TWYWENLLKICVFIFAFIMPILIITV
(δ-OR)   GVPIMVMAVTQ   PRDEAVVCMLQFPSP  SWYWDTVTKICVELFAFVPILIITV
(κ-OR)   GISAIVLGGTKVREDVDVIECSLQFPDDEYSWWDLFMKICVFVFAFVIPVLIIIV

VI
LC132    CYSLMIRRLRGVRLLSGSREKDRNLRRITRLVLVVVAVFVGCWTPVQVFVLVQGL
(μ-OR)   CYGLMILRLKSVRMLSGSKKKDRNLRRITRMVLVVVAVFIVCWTPIHIYVIIKAL
(δ-OR)   CYGLMLLRLRSVRLLSGSKKKDRSLRRITRMVLVVVGAFVVCWAPIHIFVIVWTL
(κ-OR)   CYTLMILRLKSVRLLSGSRKKDRNLRRITKLVLVVVAVFIICWTPIHIFILVEAL

VII
LC132    GVQPGSETAVAIL  RFCTALGYVHSCLNPILYAFLDENFKACFRKFCCASSLHRE
(μ-OR)   ITIPETTFQTVSW  HFCIALGYTMSCLMPVLYAFLDEMFKRCFREFCIPTSSTIE
(δ-OR)   VDINRRDPLVVAALHLCIALGYAMSSLMPVLYAFLDEMFKRCFRQLCRTPCGRQE
(κ-OR)   GSTSHSTAALSSY  YFCIALGYTMSSLMPVLYAFLDEMFKRCFRDFCFPIKMRME

LC132    MQVSDRVRTIAKDVGLGCKTSETVPRPA       367
(μ-OR)   QQNSTRVRQNTREHPSTANTVDRTNHQLENLEAETAPLP    398
(δ-OR)   PGSLRRPRQATTRERVTACTPSDGPGGAAA     372
(κ-OR)   RQSTNRVRNTVQDPASMRDVGGMNKPV        380
```

MAMMALIAN METHADONE-SPECIFIC OPIOID RECEPTOR GENE AND USES

This invention was made with government support under National Institute of Health grants R01 MH48991. The government has certain rights to this invention.

BACKGROUND OF THE INVENTION

1. Field of the Invention

This invention relates to opioid receptors from mammalian species and the genes corresponding to such receptors. Specifically, the invention relates to the isolation, cloning and sequencing of complementary DNA (cDNA) copies of messenger RNA (mRNA) encoding a novel mammalian opioid receptor gene. The invention also relates to the construction of recombinant expression constructs comprising cDNA of this novel opioid receptor gene, said recombinant expression constructs being capable of expressing opioid receptor protein in cultures of transformed prokaryotic and eukaryotic cells. Production of the receptor protein in such cultures is also provided. The invention relates to the use of such cultures of such transformed cells to produce homogeneous compositions of the novel opioid receptor protein. The invention also provides cultures of such cells producing this opioid receptor protein for the characterization of novel and useful drugs. Antibodies against and epitopes of this novel opioid receptor protein are also provided by the invention.

2. Background of the Invention

The use (and abuse) of opiates, archetypally opium and morphine, have been known since antiquity (reviewed in Brownstein, 1993, Proc. Natl. Acad. Sci. U.S.A. 90: 5391–5393). Since the nineteenth century, chemical characterization and synthesis of a number of morphine analogues have been achieved in an effort to discover a compound with the analgesic effects of morphine that lacks or is substantially attenuated in its addictive potential. These efforts have proven fruitless to date.

The biology behind the reasons why morphine and morphine-like compounds display both analgesic and addictive properties was first elucidated by the discovery of endogenous morphine-like compounds termed enkephalins (see DiChara & North, 1992, Trends in Pharmacol. Sci. 13: 185–193 for review). Accompanying this finding of an endogenous opiate was the biochemical evidence for a family of related but distinct opiate receptors, each of which displays a unique pharmacological profile of response to opiate agonists and antagonists (see McKnight & Rees, 1991, Neurotransmissions 7: 1–6 for review). To date, four distinct opiate receptors have been described by their pharmacological profiles and anatomical distribution: these comprise the $\mu$, $\delta$, $\kappa$ and $\sigma$ receptors (the $\sigma$ receptor has been determined to be a non-opioid receptor with cross-reactivity to some opioid agonists).

Thus, mammalian opioid receptors are known in the art, and some of these proteins have been isolated biochemically and their corresponding genes have been recently cloned using genetic engineering means.

Kieffer et al., 1992, Proc. Natl. Acad. Sci. U.S.A. 89: 12048–12052 disclosed the isolation of a cDNA copy of the mouse $\delta$-opioid receptor by expression cloning.

Evans et al., 1992, Science 258: 1952–1955 disclose the isolation of a cDNA copy of the mouse $\delta$-opioid receptor by expression cloning.

Chen et al., 1993, Molec. Pharmacol. 44:8–12 disclose the isolation of a cDNA copy of the rat $\mu$-opioid receptor.

Yasuda et al., 1993, Proc. Natl. Acad. Sci. U.S.A. 90: 6736–6740 disclose the isolation of a cDNA copy of each of the mouse $\kappa$- and $\delta$-opioid receptor.

Bzdega et al., 1993, Proc. Natl. Acad. Sci. U.S.A. 90: 9305–9309 disclose the isolation and chromosomal location of the $\delta$-opioid receptor in the mouse.

In 1991, U.S. pharmaceutical companies spent an estimated $7.9 billion on research and development devoted to identifying new therapeutic agents (Pharmaceutical Manufacturer's Association). The magnitude of this amount is due, in part, to the fact that the hundreds, if not thousands, of chemical compounds must be tested in order to identify a single effective therapeutic agent that does not engender unacceptable levels of undesirable or deleterious side effects. There is an increasing need for economical methods of testing large numbers of chemical compounds to quickly identify those compounds that are likely to be effective in treating disease.

This is of particular importance for psychoactive and psychotropic drugs, due to their pharmacological importance and their potential to greatly benefit or greatly harm human patients treated with such drugs. At present, few such economical systems exist. Conventional screening methods require the use of animal brain slices in binding assays as a first step. This is suboptimal for a number of reasons, including interference in the binding assay by non-specific binding of heterologous (i.e., non-receptor) cell surface proteins expressed by brain cells in such slices; differential binding by cells other than neuronal cells present in the brain slice, such as glial cells or blood cells; and the possibility that putative drug binding behavior in animal brain cells will differ from the binding behavior in human brain cells in subtle but critical ways. The ability to synthesize human opioid receptor molecules in vitro would provide an efficient and economical means for rational drug design and rapid screening of potentially useful compounds. For these and other reasons, development of in vitro screening methods for psychotropic drugs has numerous advantages and is a major research goal in the pharmaceutical industry.

SUMMARY OF THE INVENTION

The present invention relates to the cloning, expression and functional characterization of a mammalian methadone-specific opioid receptor (MSOR) gene. The invention comprises nucleic acids having a nucleotide sequence of a novel mammalian MSOR gene. The nucleic acids provided by the invention comprise a complementary DNA (cDNA) copy of the corresponding mRNA transcribed in vivo from the MSOR genes of the invention. Also provided are the deduced amino acid sequence of the cognate protein of the cDNA provided by the invention.

This invention provides nucleic acids, nucleic acid hybridization probes, recombinant eukaryotic expression constructs capable of expressing the MSOR receptors of the invention in cultures of transformed cells, such cultures of transformed eukaryotic cells that synthesize the MSOR receptors of the invention, homogeneous compositions of the MSOR receptor protein, and antibodies against and epitopes of the MSOR receptor protein of the invention. Methods for characterizing these receptor proteins and methods for using these proteins in the development of agents having pharmacological uses related to these receptors are also provided by the invention.

In a first aspect, the invention provides a nucleic acid having a nucleotide sequence encoding a mammalian methadone-specific opioid receptor. In a preferred embodiment, the nucleic acid encodes the rat MSOR receptor. In this embodiment of the invention, the nucleotide sequence includes 1452 nucleotides of the rat MSOR cDNA comprising 1101 nucleotides of coding sequence, 181 nucleotides of 5' untranslated sequence and 170 nucleotides of 3' untranslated sequence. In this embodiment of the invention, the nucleotide sequence of the MSOR receptor consists essentially of the nucleotide sequence depicted in FIGS. 1A through 1C. (SEQ ID No: 3). The use of the term "consisting essentially of" herein is meant to encompass the disclosed sequence and includes allelic variations of this nucleotide sequence, either naturally occurring or the product of in vitro chemical or genetic modification. Each such variant will be understood to have essentially the same nucleotide sequence as the nucleotide sequence of the corresponding MSOR disclosed herein.

The corresponding MSOR protein molecule, having the deduced amino acid sequence consisting essentially of the sequence shown in FIGS. 1A through 1C. (SEQ ID No.: 4), is also claimed as an aspect of the invention. The use of the term "consisting essentially of" herein is as described above. Similarly, the MSOR protein molecule, having the deduced amino acid sequence consisting essentially of the sequence shown in FIGS. 1A through 1C. (SEQ ID No.: 4), is also claimed as an aspect of the invention. MSOR protein molecules provided by the invention are understood to have substantially the same biological properties as the MSOR protein molecule encoded by the nucleotide sequence described herein.

In another aspect, the invention comprises a homogeneous composition of the 47 KD mammalian MSOR transporter or derivative thereof, said size being understood to be the size of the protein before any post-translational modifications thereof. The amino acid sequence of the MSOR transporter or derivative thereof preferably consists essentially of the amino acid sequence of the MSOR transporter protein shown in FIGS. 1A through 1C. (SEQ ID No: 4).

This invention provides both nucleotide and amino acid probes derived from the sequences herein provided. The invention includes probes isolated from either cDNA or genomic DNA, as well as probes made synthetically with the sequence information derived therefrom. The invention specifically includes but is not limited to oligonucleotide, nick-translated, random primed, or in vitro amplified probes made using cDNA or genomic clone embodying the invention, and oligonucleotide and other synthetic probes synthesized chemically using the nucleotide sequence information of cDNA or genomic clone embodiments of the invention.

It is a further object of this invention to provide such nucleic acid hybridization probes to determine the pattern, amount and extent of expression of the MSOR receptor gene in various tissues of mammals, including humans. It is also an object of the present invention to provide nucleic acid hybridization probes derived from the sequences of mammalian MSOR receptor genes of the invention to be used for the detection and diagnosis of genetic diseases. It is an object of this invention to provide nucleic acid hybridization probes derived from the DNA sequences of the mammalian MSOR receptor genes herein disclosed to be used for the detection of novel related receptor genes.

The present invention also includes synthetic peptides made using the nucleotide sequence information comprising the cDNA embodiments of the invention. The invention includes either naturally occurring or synthetic peptides which may be used as antigens for the production of MSOR receptor-specific antibodies, or useful as competitors of MSOR receptor molecules for agonist, antagonist or drug binding, or to be used for the production of inhibitors of the binding of agonists or antagonists or analogues thereof to such MSOR receptor molecules.

The present invention also provides antibodies against and epitopes of the mammalian MSOR receptor molecules of the invention. It is an object of the present invention to provide antibodies that are immunologically reactive to the MSOR receptors of the invention. It is a particular object to provide monoclonal antibodies against these MSOR receptors. Hybridoma cell lines producing such antibodies are also objects of the invention. It is envisioned at such hybridoma cell lines may be produced as the result of fusion between a non-immunoglobulin producing mouse myeloma cell line and spleen cells derived from a mouse immunized with a cell line which expresses antigens or epitopes of a mammalian MSOR receptor of the invention. The present invention also provides hybridoma cell lines that produces such antibodies, and can be injected into a living mouse to provide an ascites fluid from the mouse that is comprised of such antibodies. It is a further object of the invention to provide immunologically-active epitopes of the mammalian MSOR receptor proteins of the invention. Chimeric antibodies immunologically reactive against the MSOR receptor proteins of the invention are also within the scope of this invention.

The present invention provides recombinant expression constructs comprising a nucleic acid encoding a mammalian MSOR receptor of the invention wherein the construct is capable of expressing the encoded MSOR receptor in cultures of cells transformed with the construct. Preferred embodiments of such constructs comprise the MSOR receptor cDNA depicted in FIGS. 1A through 1C. (SEQ ID No.: 3), such constructs being capable of expressing the MSOR receptor encoded therein in cells transformed with the construct.

The invention also provides cultured cells transformed with the recombinant expression constructs of the invention, each such cultures being capable of and in fact expressing the mammalian MSOR receptor encoded in the transforming construct.

The present invention also includes within its scope protein preparations of prokaryotic and eukaryotic cell membranes containing the MSOR receptor protein of the invention, derived from cultures of prokaryotic or eukaryotic cells, respectively, transformed with the recombinant expression constructs of the invention.

The invention also provides methods for screening compounds for their ability to inhibit, facilitate or modulate the biochemical activity of the mammalian MSOR receptor molecules of the invention, for use in the in vitro screening of novel agonist and antagonist compounds. In preferred embodiments, cells transformed with a recombinant expression construct of the invention are contacted with such a compound, and the binding capacity of the compounds, as well as the effect of the compound on binding of other, known opioid agonists and antagonists, is assayed. Additional preferred embodiments comprise quantitative analyses of such effects.

The present invention is also useful for the detection of analogues, agonists or antagonists, known or unknown, of the mammalian MSOR receptors of the invention, either naturally occurring or embodied as a drug. In preferred embodiments, such analogues, agonists or antagonists may be detected in blood, saliva, semen, cerebrospinal fluid, plasma, lymph, or any other bodily fluid.

Specific preferred embodiments of the present invention will become evident from the following more detailed description of certain preferred embodiments and the claims.

DESCRIPTION OF THE DRAWINGS

FIG. 1 illustrates the nucleotide (SEQ ID No.: 3) and amino acid (SEQ ID No.: 4) sequences of the rat methadone-specific opioid receptor.

FIGS. 2A and 2B, presents an amino acid sequence comparison between the rat methadone-specific opioid receptor protein (LC132, SEQ ID No.: 4) and the rat μ-opioid receptor SEQ ID No.: 5) and the mouse δ- and κ-opioid receptor proteins (SEQ ID No.: 6, SEQ ID No.: 7).

DETAILED DESCRIPTION OF THE PREFERRED EMBODIMENTS

Figure 3A:
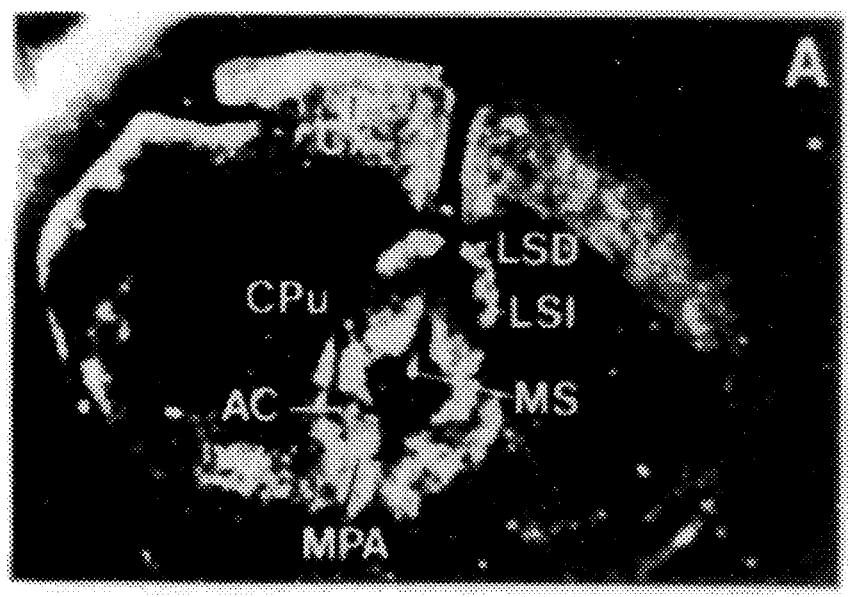
FIG. 3 illustrates in situ hybridization of rat brain sections with a nucleic acid hybridization probe specific for the methadone-specific mammalian opiod receptor of the invention.

The term "mammalian methadone-specific opioid receptor (MSOR)" as used herein refers to proteins consisting essentially of, and having substantially the same biological activity as, the protein encoded by the nucleic acid depicted in FIGS. 1A through 1C. (SEQ ID No.: 3). This definition is intended to encompass natural allelic variations in the disclosed MSOR sequence. Cloned nucleic acid provided by the present invention may encode MSOR protein of any species of origin, including, for example, mouse, rat, rabbit, cat, and human, but preferably the nucleic acid provided by the invention encodes MSOR receptors of mammalian, most preferably rat and human, origin.

The nucleic acid hybridization probes provided by the invention comprise DNA or RNA consisting essentially of the nucleotide sequence of the MSOR receptor, depicted in FIGS. 1A through 1C. (SEQ ID No.: 3), or any portion thereof effective in nucleic acid hybridization. Mixtures of such nucleic acid hybridization probes are also within the scope of this embodiment of the invention. Nucleic acid probes as provided herein are useful for detecting MSOR receptor gene expression in cells and tissues using techniques well-known in the art, including but not limited to Northern blot hybridization, in situ hybridization and Southern hybridization to reverse transcriptase-polymerase chain reaction product DNAs. The probes provided by the present invention, including oligonucleotides probes derived therefrom, are useful are also useful for Southern hybridization of mammalian, preferably human, genomic DNA for screening for restriction fragment length polymorphism (RFLP) associated with certain genetic disorders.

The production of proteins such as the MSOR receptor molecule from cloned genes by genetic engineering means is well known in this art. The discussion which follows is accordingly intended as an overview of this field, and is not intended to reflect the full state of the art.

DNA encoding an MSOR receptor may be obtained, in view of the instant disclosure, by chemical synthesis, by screening reverse transcripts of mRNA from appropriate cells or cell line cultures, by screening genomic libraries from appropriate cells, or by combinations of these procedures, as illustrated below. Screening of mRNA or genomic DNA may be carried out with oligonucleotide probes generated from the nucleic acid sequence information from the MSOR receptor disclosed herein. Probes may be labeled with a detectable group such as a fluorescent group, a radioactive atom or a chemiluminescent group in accordance with know procedures and used in conventional hybridization assays, as described in greater detail in the Examples below. In the alternative, amino acid transporter-derived nucleic acid sequences may be obtained by use of the polymerase chain reaction (PCR) procedure, using PCR oligonucleotide primers corresponding to nucleic acid sequence information derived from an MSOR receptor as provided herein. See U.S. Pat. No. 4,683,195 to Mullis et al. and U.S. Pat. No. 4,683,202 to Mullis.

The MSOR receptor protein may be synthesized in host cells transformed with a recombinant expression construct comprising a nucleic acid encoding the MSOR receptor cDNA. Such recombinant expression constructs can also be comprised of a vector that is a replicable DNA construct. Vectors are used herein either to amplify DNA encoding an MSOR receptor and/or to express DNA encoding an MSOR receptor gene. For the purposes of this invention, a recombinant expression construct is a replicable DNA construct in which a nucleic acid encoding an MSOR receptor is operably linked to suitable control sequences capable of effecting the expression of the MSOR receptor in a suitable host.

The need for such control sequences will vary depending upon the host selected and the transformation method chosen. Generally, control sequences include a transcriptional promoter, an optional operator sequence to control transcription, a sequence encoding suitable mRNA ribosomal binding sites, and sequences which control the termination of transcription and translation. Amplification vectors do not require expression control domains. All that is needed is the ability to replicate in a host, usually conferred by an origin of replication, and a selection gene to facilitate recognition of transformants. See, Sambrook et al., 1990, *Molecular Cloning: A Laboratory Manual* (Cold Spring Harbor Press: New York).

Vectors useful for practicing the present invention include plasmids, viruses (including phage), retroviruses, and integratable DNA fragments (i.e., fragments integratable into the host genome by homologous recombination). The vector replicates and functions independently of the host genome, or may, in some instances, integrate into the genome itself. Suitable vectors will contain replicon and control sequences which are derived from species compatible with the intended expression host. A preferred vector is RcRVS (Invitrogen, San Diego, Calif.). Transformed host cells are cells which have been transformed or transfected with recombinant expression constructs made using recombinant DNA techniques and comprising nucleic acid encoding an amino acid transporter protein. Preferred host cells are COS-7 cells (Gluzman, 1981, Cell 23: 175–182) and Ltk⁻ cells. Transformed host cells may express the MSOR receptor protein, but host cells transformed for purposes of cloning or amplifying nucleic acid hybridization probe DNA need not express the transporter. When expressed, the MSOR receptor of the invention will typically be located in the host cell membrane. See, Sambrook et al., ibid.

Cultures of cells derived from multicellular organisms are a desirable host for recombinant MSOR receptor protein synthesis. In principal, any higher eukaryotic cell culture is useful, whether from vertebrate or invertebrate culture. However, mammalian cells are preferred, as illustrated in the Examples. Propagation of such cells in cell culture has become a routine procedure. See *Tissue Culture*, Academic Press, Kruse & Patterson, editors (1973). Examples of useful host cell lines are human 293 cells, VERO and HeLa cells, Chinese hamster ovary (CHO) cell lines, mouse Ltk⁻ cell lines and WI138, BHK, COS-7, CV, and MDCK cell lines. COS-7 cells and Ltk⁻ cells are preferred.

The invention provides homogeneous compositions of mammalian methadone-specific opioid receptor protein produced by transformed eukaryotic cells as provided herein. Each such homogeneous composition is intended to be comprised of the MSOR receptor protein that comprises at least 90% of the protein in such a homogenous composition. The invention also provides membrane preparations from cells expressing the MSOR receptor protein as the result of transformation with a recombinant expression construct, as described herein.

Mammalian methadone-specific opioid receptor proteins made from cloned genes in accordance with the present invention may be used for screening opioid analogues, or agonists or antagonists of opioid binding, or for determining the amount of such agonists or antagonists are present in a solution of interest (e.g., blood plasma, cerebrospinal fluid or serum). For example, host cells may be transformed with a recombinant expression construct of the present invention, a mammalian MSOR receptor expressed in those host cells, and the cells or membranes thereof used to screen compounds for their effect on opioid agonist binding activity. By selection of host cells that do not ordinarily express a MSOR receptor, pure preparations of membranes containing the transporter can be obtained.

The recombinant expression constructs of the present invention are useful in molecular biology to transform cells which do not ordinarily express an MSOR receptor to thereafter express this receptor. Such cells are useful as intermediates for making cell membrane preparations useful for receptor binding activity assays, which are in turn useful for drug screening. The recombinant expression constructs of the present invention thus provide a method for screening of potentially useful drugs at advantageously lower cost than conventional animal screening protocols. While not completely eliminating the need for ultimate in vivo activity and toxicology assays, the constructs and cultures of the invention provide an important first screening step for the vast number of potentially useful psychoactive drugs synthesized, discovered or extracted from natural sources each year.

The recombinant expression constructs of the present invention are useful in molecular biology to detect, isolate, characterize and identify novel endogenous opioid receptor agonists and antagonists found in plasma, serum, lymph, cerebrospinal fluid, seminal fluid, or other potential sources of such compounds. This utility thereby enables rational drug design of novel therapeutically-active drugs using currently-available techniques (see Walters, "Computer-Assisted Modeling of Drugs", in Klegerman & Groves, eds., 1993, *Pharmaceutical Biotechnology*, Interpharm Press: Buffalo Grove, Ill., pp. 165–174).

The recombinant expression constructs of the present invention may also be useful in gene therapy. Cloned genes of the present invention, or fragments thereof, may also be used in gene therapy carried out homologous recombination or site-directed mutagenesis. See generally Thomas & Capecchi, 1987, Cell 51: 503–512; Bertling, 1987, Bioscience Reports 7: 107–112; Smithies et al., 1985, Nature 317: 230–234.

Oligonucleotides of the present invention are useful as diagnostic tools for probing MSOR receptor gene expression in tissues of humans and other animals. For example, tissues are probed in situ with oligonucleotide probes carrying detectable groups by conventional autoradiographic techniques, to investigate native expression of this receptor or pathological conditions relating thereto. Further, chromosomes can be probed to investigate the presence or absence of the corresponding MSOR receptor gene, and potential pathological conditions related thereto.

The invention also provides antibodies that are immunologically reactive to the MSOR receptor protein or epitopes thereof provided by the invention. The antibodies provided by the invention may be raised, using methods well known in the art, in animals by inoculation with cells that express an MSOR receptor or epitopes thereof, cell membranes from such cells, whether crude membrane preparations or membranes purified using methods well known in the art, or purified preparations of proteins, including fusion proteins, particularly fusion proteins comprising epitopes of the MSOR receptor protein of the invention fused to heterologous proteins and expressed using genetic engineering means in bacterial, yeast or eukaryotic cells, said proteins being isolated from such cells to varying degrees of homogeneity using conventional biochemical means. Synthetic peptides made using established synthetic means in vitro and optionally conjugated with heterologous sequences of amino acids, are also encompassed in these methods to produce the antibodies of the invention. Animals that are used for such inoculations include individuals from species comprising cows, sheep, pigs, mice, rats, rabbits, hamsters, goats and primates. Preferred animals for inoculation are rodents (including mice, rats, hamsters) and rabbits. The most preferred animal is the mouse.

Cells that can be used for such inoculations, or for any of the other means used in the invention, include any cell line which naturally expresses the MSOR receptor provided by the invention, or any cell or cell line that expresses the MSOR receptor of the invention, or any epitope thereof, as a result of molecular or genetic engineering, or that has been treated to increase the expression of an endogenous or heterologous MSOR receptor protein by physical, biochemical or genetic means. Preferred cells are *E. coli* and insect SF9 cells, most preferably *E. coli* cells, that have been transformed with a recombinant expression construct of the invention encoding an MSOR receptor protein, and that express the transporter therefrom.

The present invention also provides monoclonal antibodies that are immunologically reactive with an epitope derived from an MSOR receptor of the invention, or fragment thereof, present on the surface of such cells, preferably *E. coli* cells. Such antibodies are made using methods and techniques well known to those of skill in the art. Monoclonal antibodies provided by the present invention are produced by hybridoma cell lines, that are also provided by the invention and that are made by methods well known in the art.

Hybridoma cell lines are made by fusing individual cells of a myeloma cell line with spleen cells derived from animals immunized with cells expressing an MSOR receptor of the invention, as described above. The myeloma cell lines used in the invention include lines derived from myelomas of mice, rats, hamsters, primates and humans. Preferred myeloma cell lines are from mouse, and the most preferred mouse myeloma cell line is P3X63-Ag8.653. The animals from whom spleens are obtained after immunization are rats, mice and hamsters, preferably mice, most preferably Balb/c mice. Spleen cells and myeloma cells are fused using a number of methods well known in the art, including but not limited to incubation with inactivated Sendai virus and incubation in the presence of polyethylene glycol (PEG). The most preferred method for cell fusion is incubation in the presence of a solution of 45% (w/v) PEG-1450. Monoclonal antibodies produced by hybridoma cell lines can be harvested from cell culture supernatant fluids from in vitro cell growth; alternatively, hybridoma cells can be injected subcutaneously and/or into the peritoneal cavity of an animal, most preferably a mouse, and the monoclonal antibodies obtained from blood and/or ascites fluid.

Monoclonal antibodies provided by the present invention are also produced by recombinant genetic methods well known to those of skill in the art, and the present invention encompasses antibodies made by such methods that are immunologically reactive with an epitope of an amino acid transporter of the invention. The present invention also encompasses fragments, including but not limited to F(ab) and F(ab)'$_2$ fragments, of such antibody. Fragments are produced by any number of methods, including but not limited to proteolytic cleavage, chemical synthesis or preparation of such fragments by means of genetic engineering technology. The present invention also encompasses single-chain antibodies that are immunologically reactive with an epitope of an MSOR receptor, made by methods known to those of skill in the art.

The present invention also encompasses an epitope of an MSOR receptor of the invention, comprised of sequences and/or a conformation of sequences present in the receptor molecule. This epitope may be naturally occurring, or may be the result of proteolytic cleavage of a receptor molecule and isolation of an epitope-containing peptide or may be obtained by synthesis of an epitope-containing peptide using methods well known to those skilled in the art.

The present invention also encompasses epitope peptides produced as a result of genetic engineering technology and synthesized by genetically engineered prokaryotic or eukaryotic cells.

The invention also includes chimeric antibodies, comprised of light chain and heavy chain peptides immunologically reactive to an MSOR receptor-derived epitope. The chimeric antibodies embodied in the present invention include those that are derived from naturally occurring antibodies as well as chimeric antibodies made by means of genetic engineering technology well known to those of skill in the art.

The Examples which follow are illustrative of specific embodiments of the invention, and various uses thereof. They set forth for explanatory purposes only, and are not to be taken as limiting the invention.

EXAMPLE 1

Isolation of a Mammalian Opioid Receptor Probe by Random PCR Amplification of Rat Brain-Derived cDNA Using Degenerate Oligonucleotide Primers In order to clone novel mammalian G-protein coupled receptors, cDNA prepared from RNA from different regions of rat brain was used as template for a polymerase chain reaction (PCR)-based random cloning experiment. PCR was performed using a pair of degenerate oligonucleotide primers corresponding to the putative third and seventh transmembrane regions of a mouse δ-opioid receptor (Kieffer et al., 1992, Proc. Natl. Acad. Sci. U.S.A. 89: 12048–12052; Evans et al., 1992, Science 258: 1952–1955). PCR products obtained in this experiment were characterized by nucleotide sequencing and used to isolate a full-length cDNA from a rat brain cDNA library.

The PCR amplification experiments were performed as follows. Total RNA was isolated from various rat brain regions by the guanidinium thiocyanate method (Chirgwin et al., 1979, Biochemistry 18: 5294–5299). First-strand cDNA was prepared from rat brain RNA using standard techniques (see Sambrook et al., 1990, Molecular Cloning: A Laboratory Manual, Cold Spring Harbor Press, Cold Spring Harbor Laboratory, N.Y.) using murine reverse transcriptase (BRL, Gaithersburg, Md.) and oligo-dT priming (Sambrook et al., ibid.). The rat brain cDNA preparation was then subjected to 35 cycles of PCR amplification using 500 picomoles of degenerate oligonucleotide primers having the following sequence:

Primer III (sense):

ATGAATTCAC(G/A/C/T)(A/G)T(G/C)ATGAG(C/T)GT(G/C)GAC(C/A)G(C/A)TA    (SEQ ID NO:1)

and

Primer VII (antisense):

TTGTCGAC(G/A)TA(G/A)AG(A/G)A(T/C)(G/A/C/T)GG(G/A)TT    (SEQ ID NO:2)

in 100 μl of a solution containing 50 mM Tris-HCl (pH 8.3), 2.5 mM MgCl$_2$, 0.01% gelatin, 200 μM each dNTP, and 2.5 units of Taq polymerase (Saiki et al., 1988, Science 239: 487–491). Each PCR amplification cycle consisted of incubations at 94° C. for 1 min (denaturation), 50° C. for 1.5 min (annealing), and 72° C. for 1.5 min (extension).

Amplified products of the PCR reaction were separated on a 1.0% agarose gel (see Sambrook et al., ibid.), and fragments ranging in size from 400 basepairs (bps) to 750 bp were subcloned in the plasmid vector pBluescript (Stratagene, LaJolla, Calif.). A multiplicity of bacterial colonies comprising each of the subcloned fragments were used to make bacterial colony lifts on nitrocellulose filters using conventional techniques (see Sambrook, et al., ibid.). Such filters were hybridized with a [$^{32}$P]-dCTP-labeled radioactive nucleic acid probe comprising a full-length mouse δ-opioid receptor cDNA at a concentration of 1×10$^6$ cpm/mL under low stringency hybridization conditions [35% formamide, 5X standard citrate saline (SSC; wherein 1X SSC is 0.15M NaCl /0.015M sodium citrate, pH 7.0), 5X Denhardt's solution (wherein 1X Denhardt's solution is 0.02 g/mL each of bovine serum albumin, Ficoll and polyvinylpyrrolidone)] at 37° C. overnight. After hybridization, the filters were washed in a solution of 2X SSC/0.1% sodium dodecyl sulfate (SDS) at 55 ° C. and then exposed to X-ray film (XAR-5; Eastman-Kodak, Rochester, N.Y.) for 2 days at −70° C. using tungsten-impregnated intensifying screens (DuPont-NEN, Wilmington, Del.). Plasmid DNA from hybridizing clones was purified and the nucleotide sequence of the insert cDNA determined by the dideoxynucleotide chain termination method (Sanger et al., 1977, Proc. Natl. Acad. Sci. U.S.A. 74: 5463–5467) using Sequenase® (U.S. Biochemical Corp., Cleveland, Ohio).

EXAMPLE 2

Isolation of a Novel Mammalian Opioid Receptor cDNA

One of the PCR products (termed LC132) were isolated and sequenced in this way and were found to have a high degree of homology to the mouse δ-opioid receptor sequence (Evans et al., ibid. and Kieffer et al., ibid.). A full-length cDNA clone corresponding to this PCR fragment was isolated from a cDNA library prepared in the cloning vector λgt11 comprising oligo(dT)-primed rat brain cDNA. Plaque-containing nitrocellulose filters were hybridized with a [$^{32}$P]-dCTP-labeled, randomly-primed hybridization probe consisting of a fragment of the LC132 PCR product under high stringency conditions (which were identical to the low stringency conditions described above except that the hybridization solution was 50% formamide and hybridized filters were washed at 0.5X SSC/0.1% SDS). Positively-hybridizing λgt11 clones were plaque purified (i.e., grown, replated and re-infected in bacteria until all phage plaques hybridized to the probe, indicating that all plaques arose from phage containing the same insert; see Sambrook et al., ibid.) and analyzed by restriction enzyme digestion. An open reading frame was found on a 3.1 kilobase (kb) EcoRI-digested DNA fragment and was analyzed as follows.

Nucleotide sequence analysis performed essentially as described in Example 1 revealed the sequence show in FIGS. 1A through 1C. (SEQ ID No.: 3). The putative protein product of the gene is also shown in FIGS. 1A through 1C. (SEQ ID No: 4). The sequence was found to have an open reading frame comprising 1101 nucleotides encoding a protein 367 amino acids in length, and having a predicted molecular weight of 47 kilodaltons prior to post-translational modification. The sequence immediately 5' to the proposed initiation codon was found to contain several translation termination codons in-frame with the open reading frame, supporting the assignment of the translation start site. Predicted transmembrane domains [using the algorithm of Eisenberg et al. (1984, J. Molec. Biol. 179: 125–142)] are boxed and identified by Roman numerals (I–VII), and three sites of possible N-linked glycosylation are identified in the amino-terminal portion of the protein with solid triangles. Potential protein phosphorylation sites found in predicted cytoplasmic loops are marked with an asterisk. Further, a pair of cysteine residues conserved among known opioid receptors were found in the first and second predicted extracellular loops. On the basis of this analysis, this cloned nucleic acid was determined to be a novel mammalian opioid receptor. Comparison of the amino acid sequence of the novel receptor with the amino acid sequences of other known mammalian opioid receptors supported this conclusion.

The predicted amino acid sequences of this novel opioid receptor, the rat μ-opioid receptor (Chen et al., ibid.), the mouse δ-opioid receptor (Evans et al., ibid. and Kieffer et al., ibid.) and the mouse κ-opioid receptor (Yasuda et al., ibid.) are aligned in FIGS. 2A through 2B. Overbars indicate predicted transmembrane regions I through VII in the protein product of the genes. Amino acid residues that are found in common between all four mammalian opioid receptors are presented in boldface.

Overall, the novel mammalian receptor disclosed herein had 47% overall identity with the other mammalian opioid receptors, which similarity rose to 67% when only the predicted transmembrane domains were considered. A more detailed comparison of these amino acid sequences are quantified in Table I, showing the percentage extent of homology in pairwise fashion between the different opioid receptors. Comparisons are made individually at each transmembrane domain (TMI–TMVII), as an average over all transmembrane domains (TMavg) and as the average degree of amino acid sequence homology for each protein as a whole (avg/all). In total, 145 of the 367 residues are shared with the other mammalian opioid receptors, confirming the conclusion that the novel mammalian receptor disclosed herein is an opioid receptor.

EXAMPLE 3

Construction of a Recombinant Expression Construct, DNA Transfection and Functional Expression of the Novel Mammalian Opioid Receptor In order to biochemically characterize the novel mammalian opioid receptor described in Example 2, and to confirm that it encodes a novel opioid receptor, the cDNA was cloned into a mammalian expression construct, the resulting recombinant expression construct transfected into COS-7 cells (for transient expression assays) and mouse Ltk⁻ cells (for stable expression assays), and cell membranes (COS-7) or cell lines (Ltk⁻) were generated that expressed the receptor protein in cellular membranes at the cell surface. Such cells and membranes isolated from such cells were used for biochemical characterization experiments described below.

The entire coding region of the receptor cDNA insert was amplified using PCR as described above with primers specific for sequences in the 5' and 3' untranslated sequences; such PCR primers advantageously contained restriction enzyme digestion recognition sites at the 5' termini such that digestion with said restriction enzymes allowed facile cloning of the receptor cDNA into the mammalian expression construct RcRSV (Invitrogen, San Diego, Calif.). PCR products generated in this way were subcloned in to the RcRSV vector suing conventional techniques (see Sambrook et al., ibid.) and the orientation of the inserted cDNA confirmed by restriction enzyme digestion analysis of insert-containing subclones. Such recombinant expression constructs were introduced into COS-7 cells using the calcium-phosphate precipitation technique (Chen & Okayama, 1987, Molec. Cell. Biol. 7: 2745–2752), the transfected cells allowed to express the receptor for between 24–96 hours, and then cell membranes containing the receptor were isolated. Such membranes were harvested from cells grown on 15 cm plates by pelleting the cells at 20,000 rpm in a solution of 50 mM Tris-HCl (pH 7.4). The protein concentration was adjusted to 15–80 μg/sample for each of the binding studies described below.

These recombinant expression constructs were also introduced into Ltk cells using the calcium-phosphate precipitation technique, and stably-transfected clones were selected by growth in the mammalian neomycin analog G418 (Grand Island Biological Co., Long Island, N.Y.), as the vector RcRSV contains a functional copy of a bacterial neomycin resistance gene. Stable cell lines were then selected for membrane binding studies based on mRNA expression levels of individual neomycin-resistant transfected clones determined by Northern analysis (see Sambrook et al., ibid.). Cell membranes were prepared and used as described above for COS-7 cell transfectants.

Specific binding assays using a variety of opioid receptor agonists and antagonists were performed on membranes from both transient and stable transfectants. Ligand binding experiments were performed essentially as described in Bunzow et al. [1988, Nature 336: 783–787]. In binding experiments, increasing amounts of membrane protein (from 15–80 μg) was incubated with the radioactively-labeled opioid agonist or antagonist to be tested for 120 min at 22° C. in a total volume of 1 ml. However, in these experiments no specific binding was found for the following compounds (their known receptor binding specificities are noted in parentheses): [$^3$H]-Tyr-DAla-Gly-Met-Phe-Gly-ol (DAMCO; μ-opioid receptor agonist), [$^3$H]-c[D-penicillamine$^2$, D-penicillamines$^5$, ]enkephalin (DPDPE; δ agonist), [$^3$H]-U-69,593(ε agonist), [$^3$H]-diprenorphine (μ agonist), [$^3$H]-bremacozine (κ agonist), [$^3$H]-dihydromorphine(μ agonist), [$^3$H]-ethylketocyclazocine (κ agonist) or [$^{125}$I]-β-endorphin. Although low levels of specific binding were seen using [$^3$H]-naloxone (μ antagonist), the significance of these results was compromised by the fact that untransfected COS-7 and Ltk$^-$ cells also shown endogenous low levels of specific [$^3$H]-naloxone binding.

Figure 3B:
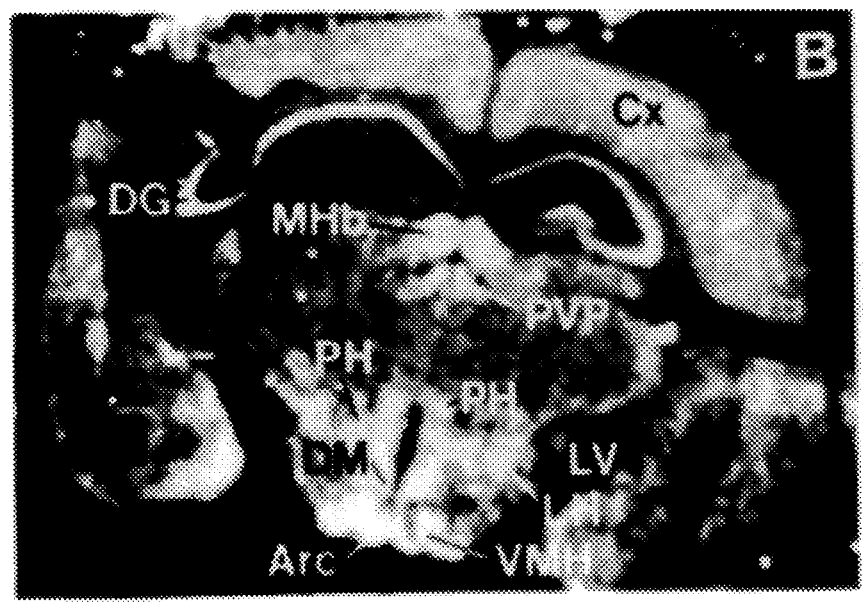
Figure 3C:
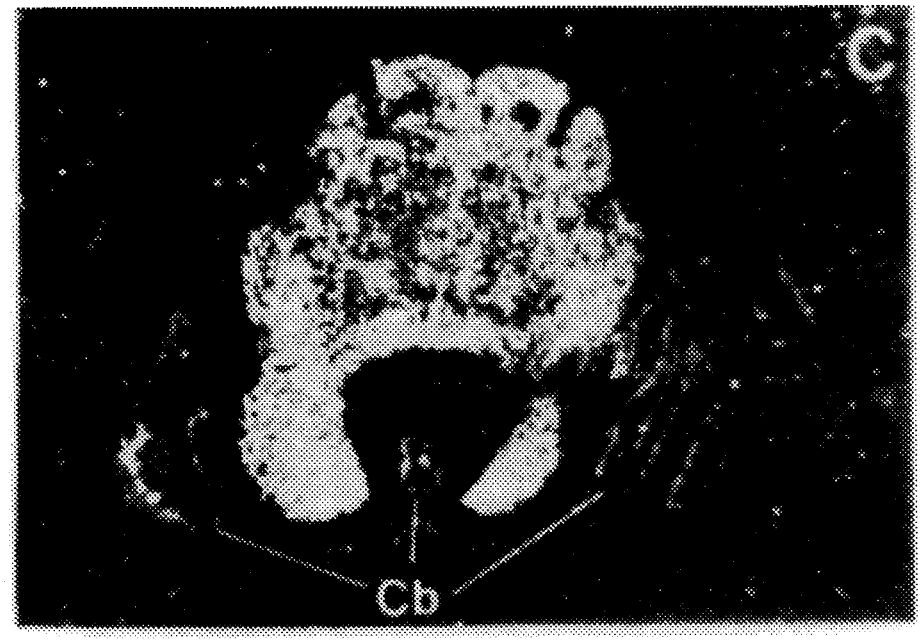
Figure 4A:
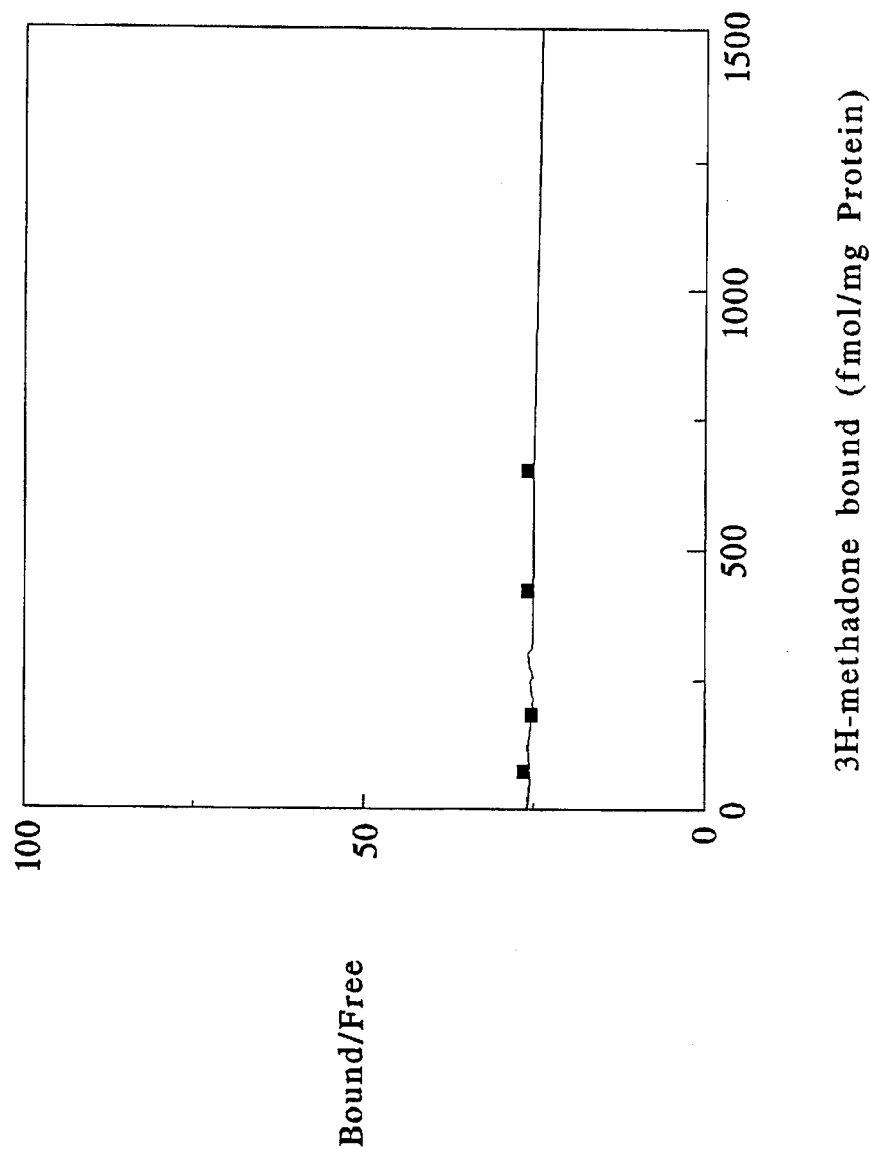
FIGS. 4A and 4B present affinity binding experiment results of $^3$H-methadone binding to COS-7 cells (FIG. 4A) and to COS-7 cells expressing the methadone-specific mammalian opiod receptor of the invention (FIG. 4B).
Figure 4B:
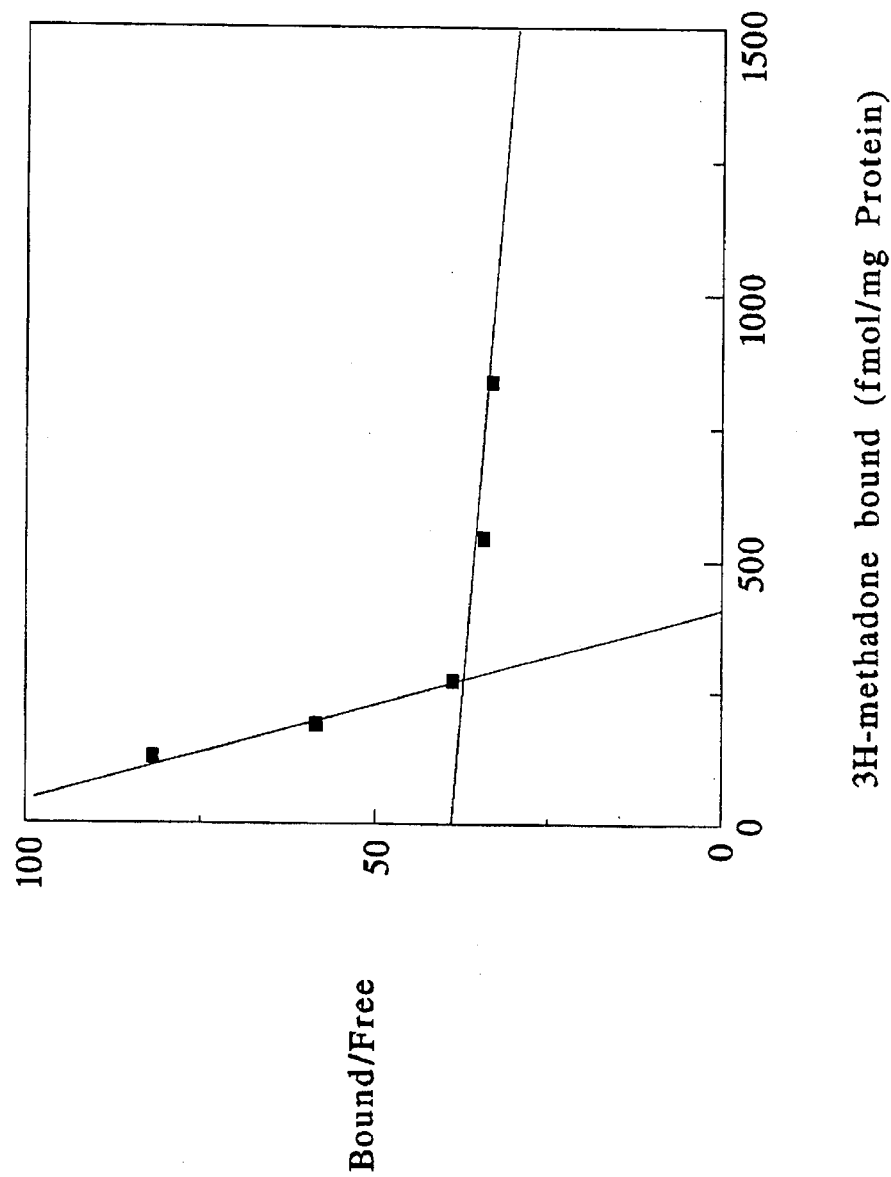

Surprisingly, however, specific binding was found using [$^3$H]-methadone. The results of Scatchard analysis of the methadone binding data are shown in FIGS. 4A and 4B. For Scatchard analysis experiments, 0.25 ml aliquots of crude plasma membrane homogenate from transfected cell cultures was incubated in duplicate with increasing concentrations of [$^3$H]methadone (70.3 Ci/mmol; 10–3000 pM final concentration) under conditions described above. The estimated value for, $B_{max}$ was derived from these data were obtained using the LIGAND computer program. FIG. 4A of FIG. 3 shows the results of radiolabeled methadone binding with untransfected COS-7 cells; similar results were found with Ltk$^-$ cell membranes. These results demonstrate no or negligible amounts of endogenous methadone binding by these cell membranes. FIG. 4B shows the results using COS-7 cells transfected with the RcRSV-LC132 expression construct. The levels of specific binding shown in this graph correspond to a dissociation constant ($K_D$) of about $10^{10}$M for methadone and a $B_{max}$ of about 400–450 femtomoles/μg protein for the novel mammalian opioid receptor expressed by these cells.

Thus, the novel mammalian opioid receptor disclosed herein has the heretofore unknown property of exhibiting specific binding to the opiate analog, methadone, while showing no specific binding to a variety of other known opioid receptor agonists and antagonists. These results support the conclusion that the receptor disclosed herein is a completely novel and heretofore unsuspected member of the opioid receptor family, termed herein therefore MSOR.

EXAMPLE 4

Brain Tissue Distribution of Methadone-Specific Opioid Receptor Expression

The distribution of mRNA corresponding to expression of the MSOR receptor gene in various regions of the rat brain was determined by in situ hybridization of rat brain slices. Rat brain sections were made and were hybridized with an [$^3$S]-CTP-labeled synthetic RNA (termed a riboprobe; see Promega Biotech Riboprobe System, Madison, Wis.) using conventional techniques.

In situ hybridization of rat brain section was performed as follows. Male Sprague-Dawley rats (200 g) were anesthetized and perfused at 40° C. with 1 L of 4% paraformaldehyde in borate buffer, pH 9.5 (fixation buffer). Brains were dissected and incubated in fixation buffer for 8 h, then further incubated overnight in fixation buffer containing 10% sucrose. Brains were then sectioned serially into series of 15 μm slices with a sliding microtome. Sections were prepared and hybridized as described in Arriza et al., 1988, Neuron 1: 887–900. A 600bp fragment of the MSOR cDNA was subcloned into a pBKS vector (Stratagene) and used to synthesize a [$^{35}$S]-CTP radiolabeled antisense cRNA probe (see Sambrook et al., ibid.) Sections were hybridized at 65° C. for 24 h with $^{35}$S-labeled probe (~1×10$^7$ cpm/ml) in 65% formamide, 0.26M NaCl, 1.3X Denhardt's solution, 13 mM Tris (pH 8.0), 1.3 mM EDTA and 13% dextran sulfate. Slides were washed in 4xSSC (0.6M NaCl, 0.06M Na citrate), digested with RNase (20 pg/ml) for 30 min at 37° C.), and then rinsed to a final stringency of 0.1X SSC at 65° C. for 30 min. Sections were dehydrated, dipped in NTB-2 emulsion, and developed after 21 days.

Results of these experiments are shown in FIG. 3. Panel A shows a section through the frontal cortex, preoptic area and caudate putamen; Panel B shows a section through the hypothalamus, thalamus and hippocampus; and Panel C shows a section through the pons and cerebellum. These experiments localized high level MSOR expression in the hypothalamus (arcuate (Arc), posterior (PH), lateral (LH) and ventromedial (VMH) hypothalamic nuclei, Panel B), certain nuclei of the thalamus (paraventricular thalamic nuclei (PVP), Panel B) , the medial habenula (MHb, Panel B), the CA regions of the hypothalamus, the dentate gyrus (DG, Panel B), the locus coeruleus and certain cortical areas (medial preoptic are (MPA), Panel A and the cortex (Cx), Panel B). Virtually no signal was seen in the caudate putamen (Cpu, Panel A) or cerebellum (Cb, Panel C). Strong hybridization was also detected in sections of the brainstem (Panel C) and the spinal cord (not shown).

These results demonstrate that the MSOR receptor disclosed herein is expressed in rat brain in a variety of anatomically-distinct sites, suggesting an important role for this receptor in both higher brain function and central nervous system control of motor and sensory nerve signalling.

EXAMPLE 5

Construction of Vaccinia Virus-Recombinant Expression Constructs for Functional Expression of the MSOR Opioid Receptor Using an alternative approach, the MSOR opioid receptor protein of the invention is expressed in human HeLa (vulval adenocarcinoma) cells via a vaccinia virus-based construct. In these experiments, the MSOR receptor cDNA of the invention is excised from the RcRSV construct and subcloned into a modified pBluescript (Strategene) vector wherein the MSOR receptor cDNA is under the control of a bacteriophage T7 RNA polymerase promoter (as is described in Blakely et al., 1991, Anal. Biochem. 194: 302–308). HeLa cells are first infected with a recombinant vaccinia virus, VTF-7, that expresses T7 RNA polymerase. Cells are incubated with virus at a concentration of about 10 plaque-forming unit/cell in serum-free Dulbecco's modified Eagle's medium at 37° C. for 30 min., and then the cells were transfected with the MSOR receptor construct described above using a lipofectin-mediated (Bethesda Research Labs, Gaithersburg, Md.) transfection protocol (see Felgner et al., 1987, Proc. Nail. Acad. Sci. U.S.A. 84: 7413–7417). Cells are then incubated for 12–24 h before being assayed for MSOR receptor expression by functional assays or Northern hybridization assays.

EXAMPLE 6

Construction of Fusion Proteins-Recombinant Expression Constructs for Expression of Immunologically-Active Epitopes of the MSOR Opioid Receptor The MSOR opioid receptor protein of the invention are expressed as fusion proteins in bacteria to produce immunologically-active epitopes. In these experiments, the MSOR opioid receptor cDNA of the invention is excised from the RcRSV construct and subcloned into a pGEX-2T construct (Pharmacia, Piscataway, N.J.) whereby the coding sequences of the MSOR receptor cDNA is translationally in-frame with sequences encoding glutathione-S-transferase (described in Arriza et al., 1992, J. Neurosci. 12: 4045–4055), or any other protein construct for which a preparative isolation method is available. After introduction of the fusion construct into bacterial cells (*E. coli*, strain D5α) using conventional techniques (see Sambrook et al., ibid.), fusion protein expression is induced with isopropyl-1-thio-β-D-galactopyranoside as described (Smith & Johnson, 1988, Gene 67: 31–40) and are purified using glutathione-Sepharose 4B (Pharmacia). Antibodies are then raised against the MSOR opioid receptor of the invention by inoculation of rabbits with 300–500 μg of purified fusion protein in Freund's adjuvant (Grand Island Biological Co., Grand Island, N.Y.), said inoculation repeated approximately every 4 weeks. Sera are immunoaffinity-purified on columns of Affi-Gel 15 derivatized with purified fusion protein. After salt elution, such antibodies are neutralized, stabilized with bovine serum albumin at a final concentration of 1 mg/mL, dialyzed against PBS and assayed by immunoblotting using conventional techniques (Harlow & Lane, 1988, *Antibodies: A Laboratory Manual*, Cold Spring Harbor Laboratory Press, Cold Spring Harbor, N.Y.).

It should be understood that the foregoing disclosure emphasizes certain specific embodiments of the invention and that all modifications or alternatives equivalent thereto are within the spirit and scope of the invention as set forth in the appended claims.

TABLE I

|  | TMI | TMII | TMIII | TMIV | TMV | TMVI | TMVII | TM avg | avg/all |
|---|---|---|---|---|---|---|---|---|---|
| LC132[a] vs rat μ[a] | 58[b] | 67 | 77 | 48 | 67 | 59 | 85 | 66 | 48 |
| LC132 vs rat κ[c] | 35 | 67 | 82 | 43 | 71 | 73 | 80 | 64 | 47 |
| LC132 vs mouse δ[d] | 46 | 67 | 77 | 52 | 63 | 59 | 75 | 63 | 46 |
| rat κ vs mouse δ | 62 | 83 | 91 | 57 | 75 | 64 | 90 | 75 | 52 |
| rat μ vs mouse δ | 69 | 90 | 86 | 48 | 83 | 77 | 85 | 77 | 51 |
| rat μ vs rat κ | 54 | 80 | 91 | 33 | 75 | 73 | 95 | 72 | 49 |

[a]Bunzow et al.
[b]percent
[c]Minami et al. (1993) FEBS Letters 329, 291.
[d]Evans et al. (1992) Science 258, 1952.

What we claim is:

1. A nucleic acid having a nucleotide sequence that encodes an amino acid sequence identified as SEQ ID No.: 4.

2. A nucleic acid hybridization probe for the detection of mammalian methadone-specific opioid receptor expression comprising the nucleotide sequence of claim 1 wherein the probe specifically binds to another nucleic acid encoding a mammalian opioid-specific receptor protein under high stringency conditions.

3. A recombinant expression construct comprising a nucleic acid having a nucleotide sequence encoding a mammalian methadone-specific opioid receptor according to claim 1, wherein the construct is capable of expressing the methadone-specific opioid receptor in a culture of eukaryotic or prokaryotic cells transformed with the construct.

4. A cell culture transformed with the recombinant expression construct of claim 3, wherein the transformed cell culture expresses the methadone-specific opoid receptor.

* * * * *

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

ATGAATTCAC NRTSATGAG Y GTSGACHGHT A      3 1

( 2 ) INFORMATION FOR SEQ ID NO:2:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

TTGTCGACRT ARRAGRA Y NG GRTT      2 4

( 2 ) INFORMATION FOR SEQ ID NO:3:

( i ) SEQUENCE CHARACTERISTICS:
        ( A ) LENGTH: 1452 base pairs ( B ) TYPE: nucleic acid
( C ) STRANDEDNESS: single
( D ) TOPOLOGY: linear ( i i ) MOLECULE TYPE: cDNA ( i x ) FEATURE:
( A ) NAME/KEY: 5'UTR
( B ) LOCATION: 1..181

( i x ) FEATURE:
( A ) NAME/KEY: CDS
( B ) LOCATION: 182..1282

( i x ) FEATURE:
( A ) NAME/KEY: 3'UTR
( B ) LOCATION: 1283..1452

( x i ) SEQUENCE DESCRIPTION: SEQ ID NO:3:

| | | | | | | |
|---|---|---|---|---|---|---|
| CCGAGGAGCC | ATTCCCAGCC | GCAGCAGACC | CCAATCTAGA | GTGAGAGTCA | TTGCTCAGTC | 60 |
| CACTGTGCTC | CTGCCTGCCC | GCCTTTCTGC | TAAGCATTGG | GGTCTATTTT | GCGCCCAGCT | 120 |
| TCTGAAGAGG | CTGTGTGTGC | CGTTGGAGGA | ACTGTACTGA | GTGGCTTTGC | AGGGTGACAG | 180 |

```
C ATG GAG TCC CTC TTT CCT GCT CCA TAC TGG GAG GTC TTG CAT GGC              226
  Met Glu Ser Leu Phe Pro Ala Pro Tyr Trp Glu Val Leu His Gly
  1               5                   10                  15

AGC CAC TTT CAA GGG AAC CTG TCC CTC CTA AAT GAG ACC GTA CCC CAC            274
Ser His Phe Gln Gly Asn Leu Ser Leu Leu Asn Glu Thr Val Pro His
            20                  25                  30

CAC CTG CTC CTC AAT GCT AGT CAC AGC GCC TTC CTG CCC CTT GGA CTC            322
His Leu Leu Leu Asn Ala Ser His Ser Ala Phe Leu Pro Leu Gly Leu
        35                  40                  45

AAG GTC ACC ATC GTG GGG CTC ATC TTG GCT GTG TGC ATC GGG GGG CTC            370
Lys Val Thr Ile Val Gly Leu Ile Leu Ala Val Cys Ile Gly Gly Leu
    50                  55                  60

CTG GGG AAC TGC CTC GTC ATG TAT GTC ATC CTC AGG ACA CCC AAG ATG            418
Leu Gly Asn Cys Leu Val Met Tyr Val Ile Leu Arg Thr Pro Lys Met
65                  70                  75

AAG ACA GCT ACC AAC ATT TAC ATA TTT AAT CTG GCA CTG GCT GAT ACC            466
Lys Thr Ala Thr Asn Ile Tyr Ile Phe Asn Leu Ala Leu Ala Asp Thr
80                  85                  90                  95

CTG GTC TTG CTA ACA CTG CCC TTC CAG GGC ACA GAC ATC CTA CTG GGC            514
Leu Val Leu Leu Thr Leu Pro Phe Gln Gly Thr Asp Ile Leu Leu Gly
            100                 105                 110

TTC TGG CCA TTT GGG AAA GCA CTC TGC AAG ACT GTC ATT GCT ATC GAC            562
Phe Trp Pro Phe Gly Lys Ala Leu Cys Lys Thr Val Ile Ala Ile Asp
        115                 120                 125

TAC TAC AAC ATG TTT ACC AGC ACT TTT ACT CTG ACC GCC ATG AGC GTA            610
Tyr Tyr Asn Met Phe Thr Ser Thr Phe Thr Leu Thr Ala Met Ser Val
    130                 135                 140

GAC CGC TAT GTG GCT ATC TGC CAC CCT ATC CGT GCC CTT GAT GTT CGG            658
Asp Arg Tyr Val Ala Ile Cys His Pro Ile Arg Ala Leu Asp Val Arg
145                 150                 155

ACA TCC AGC AAA GCC CAG GCT GTT AAT GTG GCC ATA TGG GCC CTG GCT            706
Thr Ser Ser Lys Ala Gln Ala Val Asn Val Ala Ile Trp Ala Leu Ala
160                 165                 170                 175

TCA GTG GTT GGT GTT CCT GTT GCC ATC ATG GGT TCA GCA CAA GTG GAA            754
Ser Val Val Gly Val Pro Val Ala Ile Met Gly Ser Ala Gln Val Glu
            180                 185                 190

GAT GAA GAG ATC GAG TGC CTG GTG GAG ATC CCT GCC CCT CAG GAC TAT            802
Asp Glu Glu Ile Glu Cys Leu Val Glu Ile Pro Ala Pro Gln Asp Tyr
        195                 200                 205

TGG GGC CCT GTA TTC GCC ATC TGC ATC TTC CTT TTT TCC TTC ATC ATC            850
```

|  |  |  |  |  |  |  |  |  |  |  |  |  |  |  |  |
|---|---|---|---|---|---|---|---|---|---|---|---|---|---|---|---|
| Trp | Gly | Pro<br>210 | Val | Phe | Ala | Ile | Cys<br>215 | Ile | Phe | Leu | Phe | Ser<br>220 | Phe | Ile | Ile |

| CCT | GTG | CTG | ATC | ATC | TCT | GTC | TGC | TAC | AGC | CTC | ATG | ATT | CGA | CGA | CTT | 898 |
|---|---|---|---|---|---|---|---|---|---|---|---|---|---|---|---|---|
| Pro | Val<br>225 | Leu | Ile | Ile | Ser | Val<br>230 | Cys | Tyr | Ser | Leu | Met<br>235 | Ile | Arg | Arg | Leu | |

| CGT | GGT | GTC | CGT | CTG | CTT | TCA | GGC | TCC | CGG | GAG | AAG | GAC | CGA | AAC | CTG | 946 |
| Arg<br>240 | Gly | Val | Arg | Leu | Leu<br>245 | Ser | Gly | Ser | Arg | Glu<br>250 | Lys | Asp | Arg | Asn | Leu<br>255 | |

| CGG | CGT | ATC | ACT | CGA | CTG | GTG | CTG | GTA | GTG | GTG | GCT | GTG | TTT | GTG | GGC | 994 |
| Arg | Arg | Ile | Thr | Arg<br>260 | Leu | Val | Leu | Val | Val<br>265 | Val | Ala | Val | Phe | Val<br>270 | Gly | |

| TGC | TGG | ACG | CCT | GTG | CAG | GTG | TTT | GTC | CTG | GTT | CAA | GGA | CTG | GGT | GTT | 1042 |
| Cys | Trp | Thr | Pro<br>275 | Val | Gln | Val | Phe | Val<br>280 | Leu | Val | Gln | Gly | Leu<br>285 | Gly | Val | |

| CAG | CCA | GGT | AGT | GAG | ACT | GCA | GTT | GCC | ATC | CTG | CGC | TTC | TGC | ACA | GCC | 1090 |
| Gln | Pro | Gly<br>290 | Ser | Glu | Thr | Ala | Val<br>295 | Ala | Ile | Leu | Arg | Phe<br>300 | Cys | Thr | Ala | |

| CTG | GGC | TAT | GTC | AAC | AGT | TGT | CTC | AAT | CCC | ATT | CTC | TAT | GCT | TTC | CTG | 1138 |
| Leu | Gly | Tyr<br>305 | Val | Asn | Ser | Cys | Leu<br>310 | Asn | Pro | Ile | Leu | Tyr<br>315 | Ala | Phe | Leu | |

| GAT | GAG | AAC | TTC | AAG | GCC | TGC | TTT | AGA | AAG | TTC | TGC | TGT | GCT | TCA | TCC | 1186 |
| Asp<br>320 | Glu | Asn | Phe | Lys | Ala<br>325 | Cys | Phe | Arg | Lys | Phe<br>330 | Cys | Cys | Ala | Ser | Ser<br>335 | |

| CTG | CAC | CGG | GAG | ATG | CAG | GTT | TCT | GAT | CGT | GTG | CGG | ACG | ATT | GCC | AAG | 1234 |
| Leu | His | Arg | Glu | Met<br>340 | Gln | Val | Ser | Asp | Arg<br>345 | Val | Arg | Thr | Ile | Ala<br>350 | Lys | |

| GAT | GTT | GGC | CTT | GGT | TGC | AAG | ACT | TCT | GAG | ACA | GTA | CCA | CGG | CCA | GCA | 1282 |
| Asp | Val | Gly | Leu<br>355 | Gly | Cys | Lys | Thr | Ser<br>360 | Glu | Thr | Val | Pro | Arg<br>365 | Pro | Ala | |

| TGACTAGGCG | TGGACCTGCC | CATGGTGCCT | GTCAGCCAC | AGAGCCCATC | CTACACCCAA | 1342 |
|---|---|---|---|---|---|---|
| CACGGAGCTC | ACACAGGTCA | CTGCTCTCTA | GGTTGACCCT | GAACCTTGAG | CATCTGGAGC | 1402 |
| CTTGAATGGC | TTTTCTTTTG | GATCAGGATG | CTCAGTCCTA | GAGGAAGACC | | 1452 |

( 2 ) INFORMATION FOR SEQ ID NO:4:

( i ) SEQUENCE CHARACTERISTICS:
        ( A ) LENGTH: 367 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| Met<br>1 | Glu | Ser | Leu | Phe<br>5 | Pro | Ala | Pro | Tyr | Trp<br>10 | Glu | Val | Leu | His | Gly<br>15 | Ser |
|---|---|---|---|---|---|---|---|---|---|---|---|---|---|---|---|
| His | Phe | Gln | Gly<br>20 | Asn | Leu | Ser | Leu | Leu<br>25 | Asn | Glu | Thr | Val | Pro<br>30 | His | His |
| Leu | Leu | Leu<br>35 | Asn | Ala | Ser | His | Ser<br>40 | Ala | Phe | Leu | Pro | Leu<br>45 | Gly | Leu | Lys |
| Val | Thr<br>50 | Ile | Val | Gly | Leu | Ile<br>55 | Leu | Ala | Val | Cys | Ile<br>60 | Gly | Gly | Leu | Leu |
| Gly<br>65 | Asn | Cys | Leu | Val | Met<br>70 | Tyr | Val | Ile | Leu | Arg<br>75 | Thr | Pro | Lys | Met | Lys<br>80 |
| Thr | Ala | Thr | Asn | Ile<br>85 | Tyr | Ile | Phe | Asn | Leu<br>90 | Ala | Leu | Ala | Asp | Thr<br>95 | Leu |
| Val | Leu | Leu | Thr<br>100 | Leu | Pro | Phe | Gln | Gly<br>105 | Thr | Asp | Ile | Leu | Leu<br>110 | Gly | Phe |
| Trp | Pro | Phe<br>115 | Gly | Lys | Ala | Leu | Cys<br>120 | Lys | Thr | Val | Ile | Ala<br>125 | Ile | Asp | Tyr |

| Tyr | Asn | Met | Phe | Thr | Ser | Thr | Phe | Thr | Leu | Thr | Ala | Met | Ser | Val | Asp |
| | | 130 | | | | 135 | | | | 140 | | | | | |

| Arg | Tyr | Val | Ala | Ile | Cys | His | Pro | Ile | Arg | Ala | Leu | Asp | Val | Arg | Thr |
| 145 | | | | | 150 | | | | | 155 | | | | | 160 |

| Ser | Ser | Lys | Ala | Gln | Ala | Val | Asn | Val | Ala | Ile | Trp | Ala | Leu | Ala | Ser |
| | | | | 165 | | | | | 170 | | | | | 175 | |

| Val | Val | Gly | Val | Pro | Val | Ala | Ile | Met | Gly | Ser | Ala | Gln | Val | Glu | Asp |
| | | | 180 | | | | | 185 | | | | | 190 | | |

| Glu | Glu | Ile | Glu | Cys | Leu | Val | Glu | Ile | Pro | Ala | Pro | Gln | Asp | Tyr | Trp |
| | | | 195 | | | | 200 | | | | | 205 | | | |

| Gly | Pro | Val | Phe | Ala | Ile | Cys | Ile | Phe | Leu | Phe | Ser | Phe | Ile | Ile | Pro |
| | | 210 | | | | 215 | | | | | 220 | | | | |

| Val | Leu | Ile | Ile | Ser | Val | Cys | Tyr | Ser | Leu | Met | Ile | Arg | Arg | Leu | Arg |
| 225 | | | | | 230 | | | | | 235 | | | | | 240 |

| Gly | Val | Arg | Leu | Leu | Ser | Gly | Ser | Arg | Glu | Lys | Asp | Arg | Asn | Leu | Arg |
| | | | | 245 | | | | | 250 | | | | | 255 | |

| Arg | Ile | Thr | Arg | Leu | Val | Leu | Val | Val | Ala | Val | Phe | Val | Gly | Cys |
| | | | 260 | | | | | 265 | | | | | 270 | | |

| Trp | Thr | Pro | Val | Gln | Val | Phe | Val | Leu | Val | Gln | Gly | Leu | Gly | Val | Gln |
| | | 275 | | | | | 280 | | | | | 285 | | | |

| Pro | Gly | Ser | Glu | Thr | Ala | Val | Ala | Ile | Leu | Arg | Phe | Cys | Thr | Ala | Leu |
| | 290 | | | | | 295 | | | | | 300 | | | | |

| Gly | Tyr | Val | Asn | Ser | Cys | Leu | Asn | Pro | Ile | Leu | Tyr | Ala | Phe | Leu | Asp |
| 305 | | | | | 310 | | | | | 315 | | | | | 320 |

| Glu | Asn | Phe | Lys | Ala | Cys | Phe | Arg | Lys | Phe | Cys | Cys | Ala | Ser | Ser | Leu |
| | | | | 325 | | | | | 330 | | | | | 335 | |

| His | Arg | Glu | Met | Gln | Val | Ser | Asp | Arg | Val | Arg | Thr | Ile | Ala | Lys | Asp |
| | | | 340 | | | | | 345 | | | | | 350 | | |

| Val | Gly | Leu | Gly | Cys | Lys | Thr | Ser | Glu | Thr | Val | Pro | Arg | Pro | Ala |
| | | | 355 | | | | | 360 | | | | | 365 | | |

( 2 ) INFORMATION FOR SEQ ID NO:5:

( i ) SEQUENCE CHARACTERISTICS:
        ( A ) LENGTH: 398 amino acids
        ( B ) TYPE: amino acid
        ( D ) TOPOLOGY: linear ( i i ) MOLECULE TYPE: protein ( i x ) FEATURE:
        ( A ) NAME/KEY: Protein
        ( B ) LOCATION: 1..398
        ( D ) OTHER INFORMATION: /label=Identifier
           / note= "Rat Mu-Opioid Receptor"

( x i ) SEQUENCE DESCRIPTION: SEQ ID NO:5:

| Met | Asp | Ser | Ser | Thr | Gly | Pro | Gly | Asn | Thr | Ser | Asp | Cys | Ser | Asp | Pro |
| 1 | | | | 5 | | | | | 10 | | | | | 15 | |

| Leu | Ala | Gln | Ala | Ser | Cys | Ser | Pro | Ala | Pro | Gly | Ser | Trp | Leu | Asn | Leu |
| | | | 20 | | | | | 25 | | | | | 30 | | |

| Ser | His | Val | Asp | Gly | Asn | Gln | Ser | Asp | Pro | Cys | Gly | Leu | Asn | Arg | Thr |
| | | 35 | | | | | 40 | | | | | 45 | | | |

| Gly | Leu | Gly | Gly | Asn | Asp | Ser | Leu | Cys | Pro | Gln | Thr | Gly | Ser | Pro | Ser |
| | 50 | | | | | 55 | | | | | 60 | | | | |

| Met | Val | Thr | Ala | Ile | Thr | Ile | Met | Ala | Leu | Tyr | Ser | Ile | Val | Cys | Val |
| 65 | | | | | 70 | | | | | 75 | | | | | 80 |

| Val | Gly | Leu | Phe | Gly | Asn | Phe | Leu | Val | Met | Tyr | Val | Ile | Val | Arg | Tyr |

|     |     |     |     | 85  |     |     |     | 90  |     |     |     | 95  |     |     |
| --- | --- | --- | --- | --- | --- | --- | --- | --- | --- | --- | --- | --- | --- | --- |
| Thr | Lys | Met | Lys<br>100 | Thr | Ala | Thr | Asn | Ile<br>105 | Tyr | Ile | Phe | Asn | Leu<br>110 | Ala | Leu |
| Ala | Asp | Ala<br>115 | Leu | Ala | Thr | Ser | Thr<br>120 | Leu | Pro | Phe | Gln | Ser<br>125 | Val | Asn | Tyr |
| Leu | Met<br>130 | Gly | Thr | Trp | Pro | Phe<br>135 | Gly | Thr | Ile | Leu | Cys<br>140 | Lys | Ile | Val | Ile |
| Ser<br>145 | Ile | Asp | Tyr | Tyr | Asn<br>150 | Met | Phe | Thr | Ser | Ile<br>155 | Phe | Thr | Leu | Cys | Thr<br>160 |
| Met | Ser | Val | Asp | Arg<br>165 | Tyr | Ile | Ala | Val | Cys<br>170 | His | Pro | Val | Lys | Ala<br>175 | Leu |
| Asp | Phe | Arg | Thr<br>180 | Pro | Arg | Asn | Ala | Lys<br>185 | Ile | Val | Asn | Val | Cys<br>190 | Asn | Trp |
| Ile | Leu | Ser<br>195 | Ser | Ala | Ile | Gly | Leu<br>200 | Pro | Val | Met | Phe | Met<br>205 | Ala | Thr | Thr |
| Lys | Tyr<br>210 | Arg | Gln | Gly | Ser | Ile<br>215 | Asp | Cys | Thr | Leu | Thr<br>220 | Phe | Ser | His | Pro |
| Thr<br>225 | Trp | Tyr | Trp | Glu | Asn<br>230 | Leu | Leu | Lys | Ile | Cys<br>235 | Val | Phe | Ile | Phe | Ala<br>240 |
| Phe | Ile | Met | Pro | Ile<br>245 | Leu | Ile | Ile | Thr | Val<br>250 | Cys | Tyr | Gly | Leu | Met<br>255 | Ile |
| Leu | Arg | Leu | Lys<br>260 | Ser | Val | Arg | Met | Leu<br>265 | Ser | Gly | Ser | Lys | Glu<br>270 | Lys | Asp |
| Arg | Asn | Leu<br>275 | Arg | Arg | Ile | Thr | Arg<br>280 | Met | Val | Leu | Val | Val<br>285 | Val | Ala | Val |
| Phe | Ile<br>290 | Val | Cys | Trp | Thr | Pro<br>295 | Ile | His | Ile | Tyr | Val<br>300 | Ile | Ile | Lys | Ala |
| Leu<br>305 | Ile | Thr | Ile | Pro | Glu<br>310 | Thr | Thr | Phe | Gln | Thr<br>315 | Val | Ser | Trp | His | Phe<br>320 |
| Cys | Ile | Ala | Leu | Gly<br>325 | Tyr | Thr | Asn | Ser | Cys<br>330 | Leu | Asn | Pro | Val | Leu<br>335 | Tyr |
| Ala | Phe | Leu | Asp<br>340 | Glu | Asn | Phe | Lys | Arg<br>345 | Cys | Phe | Arg | Glu | Phe<br>350 | Cys | Ile |
| Pro | Thr | Ser<br>355 | Ser | Thr | Ile | Glu | Gln<br>360 | Gln | Asn | Ser | Thr | Arg<br>365 | Val | Arg | Gln |
| Asn | Thr<br>370 | Arg | Glu | His | Pro | Ser<br>375 | Thr | Ala | Asn | Thr | Val<br>380 | Asp | Arg | Thr | Asn |
| His<br>385 | Gln | Leu | Glu | Asn | Leu<br>390 | Glu | Ala | Glu | Thr | Ala<br>395 | Pro | Leu | Pro |     |     |

( 2 ) INFORMATION FOR SEQ ID NO:6:

( i ) SEQUENCE CHARACTERISTICS:
        ( A ) LENGTH: 372 amino acids
        ( B ) TYPE: amino acid
        ( D ) TOPOLOGY: linear ( i i ) MOLECULE TYPE: protein ( i x ) FEATURE:
        ( A ) NAME/KEY: Protein
        ( B ) LOCATION: 1..372
        ( D ) OTHER INFORMATION: /label=Identifier
          / note= "Mouse Delta-Opioid Receptor"

( x i ) SEQUENCE DESCRIPTION: SEQ ID NO:6:

| Met<br>1 | Glu | Leu | Val | Pro<br>5 | Ser | Ala | Arg | Ala | Glu<br>10 | Leu | Gln | Ser | Ser | Pro<br>15 | Leu |
| --- | --- | --- | --- | --- | --- | --- | --- | --- | --- | --- | --- | --- | --- | --- | --- |

```
Val  Asn  Leu  Ser  Asp  Ala  Phe  Pro  Ser  Ala  Phe  Pro  Ser  Ala  Gly  Ala
               20                  25                       30

Asn  Ala  Ser  Gly  Ser  Pro  Gly  Ala  Arg  Ser  Ala  Ser  Ser  Leu  Ala  Leu
          35                       40                  45

Ala  Ile  Ala  Ile  Thr  Ala  Leu  Tyr  Ser  Ala  Val  Cys  Ala  Val  Gly  Leu
     50                       55                  60

Ile  Gly  Asn  Val  Leu  Val  Met  Leu  Gly  Ile  Val  Arg  Tyr  Thr  Lys  Leu
65                       70                  75                            80

Lys  Thr  Ala  Thr  Asn  Ile  Tyr  Ile  Phe  Asn  Leu  Ala  Leu  Ala  Asp  Ala
                    85                       90                       95

Leu  Ala  Thr  Ser  Thr  Leu  Pro  Phe  Gln  Ser  Ala  Lys  Tyr  Leu  Met  Glu
               100                      105                      110

Thr  Trp  Pro  Phe  Gly  Glu  Leu  Leu  Cys  Lys  Ala  Val  Leu  Ser  Ile  Asp
          115                      120                      125

Tyr  Tyr  Asn  Met  Phe  Thr  Ser  Ile  Phe  Thr  Leu  Thr  Met  Met  Ser  Val
          130                      135                 140

Asp  Arg  Tyr  Ile  Ala  Val  Cys  His  Pro  Val  Lys  Ala  Leu  Asp  Phe  Arg
145                      150                 155                           160

Thr  Pro  Ala  Lys  Ala  Lys  Leu  Ile  Asn  Ile  Cys  Ile  Trp  Val  Leu  Ala
               165                      170                      175

Ser  Gly  Val  Gly  Val  Pro  Ile  Met  Val  Met  Ala  Val  Thr  Gln  Pro  Arg
               180                      185                 190

Asp  Phe  Ala  Val  Val  Cys  Met  Leu  Gln  Phe  Pro  Ser  Pro  Ser  Trp  Tyr
          195                      200                 205

Trp  Asp  Thr  Val  Thr  Lys  Ile  Cys  Val  Phe  Ile  Phe  Ala  Phe  Val  Val
     210                      215                 220

Pro  Ile  Leu  Ile  Ile  Thr  Val  Cys  Tyr  Gly  Leu  Met  Leu  Leu  Arg  Leu
225                      230                 235                           240

Arg  Ser  Val  Arg  Leu  Leu  Ser  Gly  Ser  Lys  Glu  Lys  Asp  Arg  Ser  Leu
               245                      250                      255

Arg  Arg  Ile  Thr  Arg  Met  Val  Leu  Val  Val  Val  Gly  Ala  Phe  Val  Val
               260                      265                      270

Cys  Trp  Ala  Pro  Ile  His  Ile  Phe  Val  Ile  Val  Trp  Thr  Leu  Val  Asp
               275                      280                 285

Ile  Asn  Arg  Arg  Asp  Pro  Leu  Val  Val  Ala  Ala  Leu  His  Leu  Cys  Ile
     290                      295                 300

Ala  Leu  Gly  Tyr  Ala  Asn  Ser  Ser  Leu  Asn  Pro  Val  Leu  Tyr  Ala  Phe
305                      310                 315                           320

Leu  Asp  Glu  Asn  Phe  Lys  Arg  Cys  Phe  Arg  Gln  Leu  Cys  Arg  Thr  Pro
               325                      330                      335

Cys  Gly  Arg  Gln  Glu  Pro  Gly  Ser  Leu  Arg  Arg  Pro  Arg  Gln  Ala  Thr
               340                      345                      350

Thr  Arg  Glu  Arg  Val  Thr  Ala  Cys  Thr  Pro  Ser  Asp  Gly  Pro  Gly  Gly
          355                      360                 365

Gly  Ala  Ala  Ala
          370
```

( 2 ) INFORMATION FOR SEQ ID NO:7:

( i ) SEQUENCE CHARACTERISTICS:
        ( A ) LENGTH: 380 amino acids
        ( B ) TYPE: amino acid
        ( D ) TOPOLOGY: linear ( i i ) MOLECULE TYPE: protein ( i x ) FEATURE:

( A ) NAME/KEY: Protein
( B ) LOCATION: 1..380
( D ) OTHER INFORMATION: /label=Identifier
/ note= "Mouse Kappa-Opioid Receptor"

( x i ) SEQUENCE DESCRIPTION: SEQ ID NO:7:

| Met | Glu | Ser | Pro | Ile | Gln | Ile | Phe | Arg | Gly | Asp | Pro | Gly | Pro | Thr | Cys |
| 1 | | | | 5 | | | | | 10 | | | | | 15 | |

| Ser | Pro | Ser | Ala | Cys | Leu | Leu | Pro | Asn | Ser | Ser | Ser | Trp | Phe | Pro | Asn |
| | | | 20 | | | | | 25 | | | | | 30 | | |

| Trp | Ala | Glu | Ser | Asp | Ser | Asn | Gly | Ser | Val | Gly | Ser | Glu | Asp | Gln | Gln |
| | | 35 | | | | | 40 | | | | | 45 | | | |

| Leu | Glu | Ser | Ala | His | Ile | Ser | Pro | Ala | Ile | Pro | Val | Ile | Ile | Thr | Ala |
| | 50 | | | | | 55 | | | | | 60 | | | | |

| Val | Tyr | Ser | Val | Val | Phe | Val | Val | Gly | Leu | Val | Gly | Asn | Ser | Leu | Val |
| 65 | | | | | 70 | | | | | 75 | | | | | 80 |

| Met | Phe | Val | Ile | Ile | Arg | Tyr | Thr | Lys | Met | Lys | Thr | Ala | Thr | Asn | Ile |
| | | | | 85 | | | | | 90 | | | | | 95 | |

| Tyr | Ile | Phe | Asn | Leu | Ala | Leu | Ala | Asp | Ala | Leu | Val | Thr | Thr | Thr | Met |
| | | | 100 | | | | | 105 | | | | | 110 | | |

| Pro | Phe | Gln | Ser | Ala | Val | Tyr | Leu | Met | Asn | Ser | Trp | Pro | Phe | Gly | Asp |
| | | 115 | | | | | 120 | | | | | 125 | | | |

| Val | Leu | Cys | Lys | Ile | Val | Ile | Ser | Ile | Asp | Tyr | Tyr | Asn | Met | Phe | Thr |
| | 130 | | | | | 135 | | | | | 140 | | | | |

| Ser | Ile | Phe | Thr | Leu | Thr | Met | Met | Ser | Val | Asp | Arg | Tyr | Ile | Ala | Val |
| 145 | | | | | 150 | | | | | 155 | | | | | 160 |

| Cys | His | Pro | Val | Lys | Ala | Leu | Asp | Phe | Arg | Thr | Pro | Leu | Lys | Ala | Lys |
| | | | | 165 | | | | | 170 | | | | | 175 | |

| Ile | Ile | Asn | Ile | Cys | Ile | Trp | Leu | Leu | Ala | Ser | Ser | Val | Gly | Ile | Ser |
| | | | 180 | | | | | 185 | | | | | 190 | | |

| Ala | Ile | Val | Leu | Gly | Gly | Thr | Lys | Val | Arg | Glu | Asp | Val | Asp | Val | Ile |
| | | 195 | | | | | 200 | | | | | 205 | | | |

| Glu | Cys | Ser | Leu | Gln | Phe | Pro | Asp | Asp | Glu | Tyr | Ser | Trp | Trp | Asp | Leu |
| | 210 | | | | | 215 | | | | | 220 | | | | |

| Phe | Met | Lys | Ile | Cys | Val | Phe | Val | Phe | Ala | Phe | Val | Ile | Pro | Val | Leu |
| 225 | | | | | 230 | | | | | 235 | | | | | 240 |

| Ile | Ile | Ile | Val | Cys | Tyr | Thr | Leu | Met | Ile | Leu | Arg | Leu | Lys | Ser | Val |
| | | | | 245 | | | | | 250 | | | | | 255 | |

| Arg | Leu | Leu | Ser | Gly | Ser | Arg | Glu | Lys | Asp | Arg | Asn | Leu | Arg | Arg | Ile |
| | | | 260 | | | | | 265 | | | | | 270 | | |

| Thr | Lys | Leu | Val | Leu | Val | Val | Val | Ala | Val | Phe | Ile | Ile | Cys | Trp | Thr |
| | | 275 | | | | | 280 | | | | | 285 | | | |

| Pro | Ile | His | Ile | Phe | Ile | Leu | Val | Glu | Ala | Leu | Gly | Ser | Thr | Ser | His |
| | 290 | | | | | 295 | | | | | 300 | | | | |

| Ser | Thr | Ala | Ala | Leu | Ser | Ser | Tyr | Tyr | Phe | Cys | Ala | Ile | Leu | Gly | Tyr |
| 305 | | | | | 310 | | | | | 315 | | | | | 320 |

| Thr | Asn | Ser | Ser | Leu | Asn | Pro | Val | Leu | Tyr | Ala | Phe | Leu | Asp | Glu | Asn |
| | | | | 325 | | | | | 330 | | | | | 335 | |

| Phe | Lys | Arg | Cys | Phe | Arg | Asp | Phe | Cys | Phe | Pro | Ile | Lys | Met | Arg | Met |
| | | | 340 | | | | | 345 | | | | | 350 | | |

| Glu | Arg | Gln | Ser | Thr | Asn | Arg | Val | Arg | Asn | Thr | Val | Gln | Asp | Pro | Ala |
| | | 355 | | | | | 360 | | | | | 365 | | | |

| Ser | Met | Arg | Asp | Val | Gly | Gly | Met | Asn | Lys | Pro | Val |
| | 370 | | | | | 375 | | | | | 380 |